United States Patent [19]

Kühle et al.

[11] 3,980,693
[45] Sept. 14, 1976

[54] N-(TRIHALOMETHYLTHIO)-CARBAMIC ACID OXIME ESTERS

[75] Inventors: Engelbert Kühle, Bergisch Gladbach; Erich Klauke, Odenthal-Hahnenberg; Brigitte Hamburger, Cologne; Hans Scheinpflug, Leverkusen, all of Germany

[73] Assignee: Bayer Aktiengesellschaft, Leverkusen, Germany

[22] Filed: Feb. 24, 1975

[21] Appl. No.: 552,509

Related U.S. Application Data

[62] Division of Ser. No. 392,832, Aug. 29, 1973, Pat. No. 3,890,386.

[30] Foreign Application Priority Data

Sept. 6, 1972   Germany............................ 2243626

[52] U.S. Cl. .......................... 260/470; 260/453 R; 260/465 D; 260/465 E; 260/465.4; 260/465.5 R; 260/481 R; 260/566 AC; 424/304; 424/309; 424/311; 424/313; 424/327
[51] Int. Cl.² ............... C07C 149/20; C07C 149/40
[58] Field of Search .......... 260/470, 566 AC, 481 R

[56]         References Cited
            UNITED STATES PATENTS 3,576,834   4/1971   Buchanan ...................... 260/470 X

*Primary Examiner*—Lewis Gotts
*Assistant Examiner*—Dolph H. Torrence
*Attorney, Agent, or Firm*—Burgess, Dinklage & Sprung

[57]          ABSTRACT

N-(trihalomethylthio)-carbamic acid oxime ester of the formula $$R-N(S-C(Cl)_n(F)_{3-n})-C(=O)-O-N=C(R')(R'') \quad (I)$$

in which
R is alkyl; cycloalkyl; or aryl optionally carrying at least one halogen, nitro, $C_1$–$C_6$ alkyl, trifluoromethyl or $C_1$–$C_6$ alkoxy radical;
R' and R'' each independently is alkyl or alkenyl optionally substituted by an alkoxycarbonyl or amidocarbonyl radical; cycloalkyl; aryl optionally carrying at least one halogen, nitrile, nitro, trifluoromethyl, $C_1$–$C_6$ alkyl or $C_1$–$C_6$ alkoxy radical; nitrile; halogen; alkoxycarbonyl; or amidocarbonyl; or
R' and R'', conjointly with the carbon atom that links them, form a cycloalkylidene group with 5 or 6 carbon atoms optionally carrying at least one $C_1$–$C_6$ alkyl, $C_1$–$C_6$ alkylene or cycloalkyl radical; and
n is 0, 1, 2 or 3,
which possess fungicidal and microbicidal properties.

9 Claims, No Drawings

N-(TRIHALOMETHYLTHIO)-CARBAMIC ACID OXIME ESTERS

This is a division of application Ser. No. 392,832, filed Aug. 29, 1973, now U.S. Pat. No. 3,890,386.

The present invention relates to and has for its objects the provision of particular new N-(trihalomethylthio)-carbamic acid oxime esters which possess fungicidal and microbicidal properties, active compositions in the form of mixtures of such compounds with solid and liquid dispersible carrier vehicles and methods for producing such compounds and for using such compounds in a new way especially for combating pests, e.g. fungi and microbes, with other and further objects becoming apparent from a study of the within specification and accompanying examples.

It has been disclosed in German Published Specification DOS No. 2,016,623 that N-sulfenylated N-methylcarbamidoximes that are derived from N-hydroxyimidothioacetic acid esters exhibit insecticidal, acaricidal and fungicidal activities. While the insecticidal action of these known active compounds is in part satisfactory for practical use, the fungicidal potency is hardly adequate.

The present invention provides, as new compounds, the N-sulfenylated carbamidoximes of the general formula

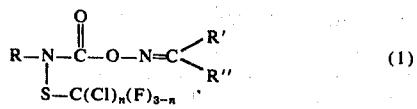
(I)

in which
R is alkyl; cycloalkyl; or aryl optionally carrying at least one halogen, nitro, $C_1-C_6$ alkyl, trifluoromethyl or $C_1-C_6$ alkoxy radical;
R' and R'' each independently is alkyl or alkenyl optionally substituted by an alkoxycarbonyl or amidocarbonyl radical; cycloalkyl; aryl optionally carrying at least one halogen, nitrile, nitro, trifluoromethyl, $C_1-C_6$ alkyl or $C_1-C_6$ alkoxy radical; nitrile; halogen; alkoxycarbonyl; or amidocarbonyl; or
R' and R'', conjointly with the carbon atom that links them, form a cycloalkylidene group with 5 or 6 carbon atoms optionally carrying at least $C_1-C_6$ alkyl, $C_1-C_6$ alkylene or cycloalkyl radical; and
$n$ is 0, 1, 2 or 3.

Preferably, R is alkyl of up to 4 carbon atoms or phenyl optionally substituted by fluorine, chlorine, nitro, methyl, trifluoromethyl or methoxy and $n$ is 1, 2 or 3. Preferably R' and R'' are each alkyl of up to 20 carbon atoms optionally substituted by alkoxycarbonyl with a total of up to 5 carbon atoms; cyclohexyl or phenyl optionally substituted by fluorine, chlorine, nitrile, nitro, methyl, trifluoromethyl or methoxy; chlorine; nitrile; alkoxycarbonyl with a total of up to 7 carbon atoms or amidocarbonyl; or R' and R'', conjointly with the carbon atom which links them, form a cyclopentylidene, cyclohexylidene or norbornylidene radical optionally substituted by at least one methyl or cyclohexyl radical.

A preferred sub-group is those compounds wherein R is methyl, phenyl or chlorophenyl; $n$ is 2 or 3; and R' and R'' each individually is alkyl optionally substituted by lower alkoxycarbonyl, lower alkoxycarbonyl, phenyl, chlorophenyl or nitrile, or R' and R'', conjointly with the carbon atom that links them, form a cyclopentylidene, cyclohexylidene or norbornylidene radical optionally substituted by cyclohexyl.

It is distinctly surprising that the compounds according to the invention display a higher fungicidal and bactericidal action than the prior-art sulfenylated methylcarbamidoximes that are derived from N-hydroxyimidothioacetic acid esters, and furthermore possess a very good microbicidal activity, which is superior to that of conventional agents, against bacteria, molds and yeasts, so that they can be used for the anti-microbial treatment of organic materials. The compounds according to the invention thus represent an enrichment of the art.

The present invention also provides a process for the preparation of an N-sulfenylated carbamidoxime of the formula (I) in which an N-sulfenylated carbamic acid fluoride of the general formula

(II)

in which
R and $n$ have the above-mentioned meanings, is reacted with an oxime of the general formula

(III), in which
R' and R'' have the above-mentioned meanings, the oxime (III) being reacted as such in the presence of a diluent and of an acid-binding agent, or in the form of an alkali metal salt thereof, in the presence of water as a diluent.

When using N-(fluorodichloromethylthio)-N-phenylcarbamic acid fluoride and α-oximinophenylacetonitrile as starting materials, the course of the reaction can be represented by the following equation:

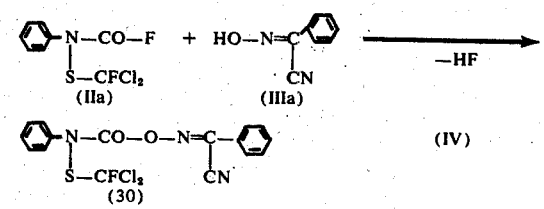

Compounds of the formula (II) are disclosed in German Published Specification DAS No. 1,297,095. In addition to the compounds described there, the following sulfenylated carbamic acid fluorides, inter alia, can also be used: N-(trifluoromethylthio)-N-methyl-carbamic acid fluoride (boiling point 100°–103°C/760 mmHg); N-(difluorochloromethylthio)-N-methylcarbamic acid fluoride (boiling point 68°–73°C/70 mmHg); N-(trichloromethylthio)-N-phenylcarbamic acid fluoride (melting point 59°–62°C); N-(fluorodichloromethylthio)-N-(2-chlorophenyl)carbamic acid fluoride (boiling point 152°–158°C/15 mmHg). These compounds are prepared in the same manner as in German DAS No. 1,297,095.

As examples of compounds of the formula (III) the oximes of the following compounds with carbonyl groups may be mentioned: acetone, diethyl ketone, isopropyl methyl ketone, pinacoline, dipropyl ketone, chloroacetone, methyl vinyl ketone, mesityl oxide, 1,1-dimethoxyacetone, cyanoacetic esters, malodinitrile, acetoacetic esters, acetoacetic acid amide, malonic acid esters, acetonedicarboxylic acid esters, cyclopentanone, cyclohexanone, camphor, acetophenone, 4-chloroacetophenone, 3-nitroacetophenone, benzalacetone, benzophenone, 4-chlorobenzophenone and methyl 4-methoxyphenyl ketone. Other suitable oximes are oximino-tert.-butyl-acetonitrile, oximino-phenyl-acetonitrile and oximino(2-chlorophenyl)-acetonitrile. The oximes can be prepared in the manner customary in the laboratory.

Possibile diluents are all inert organic solvents. These include ethers, such as diethyl ether, tetrahydrofuran and dioxane, hydrocarbons, such as benzene, and chlorinated hydrocarbons, such as chloroform and chlorobenzene.

To bind the hydrogen fluoride produced in the reaction, a tertiary amine base, such as triethylamine, or inorganic bases, such as alkali metal hydroxides or alkali metal carbonates, are added to the reaction mixture. As stated above, it is also possible directly to react the alkali metal derivatives of the oximes, in the aqueous phase.

The reaction temperatures can be varied within a fairly wide range. In general, the reaction is carried out at from 0° to 100°C, preferably at from 20° to 40°C.

In carrying out the process, equimolar amounts are generally used. In many cases it has also proved advantageous to employ the oxime reactant in a slight excess (up to 20 per cent by weight).

The reaction mixture is worked up in the usual manner. The reaction products themselves are either oils of yellow to brown color or colorless crystalline substances.

The active compounds according to the invention display a strong fungicidal and bactericidal action. They do not damage crop plants in the concentrations required for combating fungi and bacteria and have a low toxicity to warm-blooded animals. For these reasons they are suitable for use as plant-protection agents for combating fungi and bacteria. Fungitoxic agents are employed in plant protection for combating *Archimycetes, Phycomycetes, Ascomycetes, Basidiomycetes* and *Fungi Imperfecti*.

The active compounds according to the invention have a broad spectrum of action and can be used against parasitary fungi and bacteria which attack above-ground parts of plants, or attack the plants through the soil, and against seed-borne pathogens.

The active compounds according to the invention have also proved of value in combating diseases of rice. Thus they showed a very good action against the fungi *Piricularia oryzae* and *Pellicularia sasakii*, for which reason they can be employed for conjointly combating these two diseases.

However, the compounds according to the invention are also active against other fungi which attack crop plants, for example *Cochliobolus myiabeanus, Mycosphaerella musicola, Cercospora personata, Botrytis cinerea*, varieties of *Alternaria, Verticillium alboatrum,* *Phialophora cinerescens* and varieties of *Fusarium*, as well as against the bacterium *Xanthomonas oryzae*.

The compounds according to the invention are furthermore of interest as microbicides. As a result of their superior anti-microbial action, which extends over a broad range of micro-organisms, the compounds are suitable for many purposes in disinfection, preservation and antimicrobial treatment.

As micro-organisms which it is economically important to combat there should be mentioned: *Aspergillus niger, Pernicillium camerunense* and *Paecilomyces varioti* as representatives of resistant molds, and also *Trichophyton mentagrophytes* as a wide-spread foot fungus. *Candida albicans* and *Saccharomyces* spec. belong to the yeasts, which frequently occur as pathogenic forms. *Escherichia coli, Bacterium proteus, Pseudomonas pyocyanea* and *Staphylococcus aureus* belong to the Gram-negative or Gram-positive bacteria, and are in part pathogenic.

The compounds are also suitable for the preservation of wood pulp, the intermediate product for the manufacture of paper. Due to lengthy shipping transport, moist wood pulp very easily turns moldy. In part, this very moldy wood pulp is no longer usable for the manufacture of finer papers. For years, mercury compounds (for example phenyl-mercury acetate) were used widely here. Now that these compounds have been forbidden because of toxicological misgivings, the same difficulties of moldiness again arise.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g.

kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, bactericides and microbicides, or insecticides, acaricides, rodenticides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi, bacteria and microbes, and more particularly methods of combating at least one of fungi and bacteria, which comprises applying to at least one of correspondingly (a) such fungi, (b) such bacteria, (c) such microbes and (d) the corresponding habitat thereof, i.e. the locus to be protected, a correspondingly combative or toxic amount, i.e. fungicidally, bactericidally or microbicidally effective amount, of the particular active compound of the invention alone or together with a carrier vehicle as noted above. The instant formulations or compositions are applied in the usual manner, for instance by spraying, atomizing, vaporizing scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The fungicidal and microbicidal activity of the compounds of this invention is illustrated in the following test Examples.

EXAMPLE 1

Mycelium growth test
Nutrient medium used:
 20 parts by weight of agar-agar
 200 parts by weight of potato decoction
 5 parts of weight of malt
 15 parts by weight of dextrose
 5 parts by weight of peptone
 2 parts by weight of disodium phosphate
 0.3 part by weight of calcium nitrate
Proportion of solvent mixture to nutrient medium:
 2 parts by weight of solvent mixture
 100 parts by weight of agar nutrient medium
Composition of solvent mixture:
 0.19 part by weight of dimethylformamide
 0.01 part by weight of emulsifier (alkylaryl polyglycol ether)
 1.80 parts by weight of water
 2 parts by weight of solvent mixture The amount of active compound required for the desired concentration of active compound in the nutrient medium was mixed with the stated amount of solvent mixture. The concentrate was thoroughly mixed, in the stated proportion, with the liquid nutrient medium, which had been cooled to 42°C, and was poured into Petri dishes of 9 cm diameter.

Control plates, to which a preparation had not been added, were also set up.

When the nutrient medium had cooled and solidified, the plates were inoculated with the species of fungi stated in the table and incubated at about 21°C.

Evaluation was carried out after 4–10 days, dependent on the speed of growth of the fungi. When the evaluation was carried out, the radial growth of the mycelium on the treated nutrient media was compared with the growth on the control nutrient media. In the evaluation of the fungus growth, the following characteristic values were used:
 0 no fungus growth
 1 very strong inhibition of growth
 2 medium inhibition of growth
 3 slight inhibition of growth
 4 growth equal to that of untreated controls.

The active compounds, the active compound concentrations and the results can be seen from the table which follows:

Table 1

| Active compounds | Active compound concentration ppm 10 | Mycelium growth test — Fungi and bacteria | | | | | | | |
|---|---|---|---|---|---|---|---|---|---|
| | | Piricularia oryzae | Phialophora-cinerescens | Pellicularia sasakii | Mycosphaerella muscola | Verticillium alboatrum | Fusarium dianthi | Cochliobolus miyabeanus | Colletotrichum coffeanum | Xanthomonas oryae |
| $CH_3-N(S-CFCl_2)-CO-O-N=C(S-\text{phenyl-}C(CH_3)_3)(CH_3)$ (known) (A) | | 1 | 4 | 4 | 2 | 4 | 4 | 4 | 3 | 4 |
| $CH_3-N(S-CCl_3)-CO-O-N=C(S-CH_3)(CH_3)$ (known) (B) | | 4 | 4 | 4 | 4 | 4 | 4 | 4 | 4 | 4 |
| $CH_3-N(S-CFCl_2)-CO-O-N=C(\text{phenyl})(CN)$ (2) | | 0 | 0 | 1 | 0 | 0 | 2 | 0 | 0 | — |
| $\text{phenyl-}N(S-CFCl_2)-CO-O-N=C(CH_3)(CH_3)$ (1) | | 0 | 0 | 1 | 0 | 0 | 0 | 0 | 0 | 0 |
| $CH_3-N(S-CFCl_2)-CO-O-N=C(CH_3)(CO-OC_2H_5)$ (10) | | 0 | 0 | 1 | 0 | 0 | 0 | 0 | 0 | 0 |
| $\text{phenyl-}N(S-CFCl_2)-CO-O-N=C(CH_3)(CO-OC_2H_5)$ (11) | | 0 | 0 | 1 | 0 | 0 | 0 | 0 | 0 | 0 |
| $\text{phenyl-}N(S-CFCl_2)-CO-O-N=C((CH_2)_2-CO-OC_2H_5)_2$ (44) | | 0 | 2 | 0 | 2 | 1 | 0 | 0 | 0 | |
| $CH_3-N(S-CFCl_2)-CO-O-N=C(CO-OC_2H_5)_2$ (14) | | 0 | 0 | 1 | 0 | 2 | 2 | 0 | 0 | 0 |
| $\text{phenyl-}N(S-CFCl_2)-CO-O-N=C(CO-OC_2H_5)_2$ (15) | | 0 | 0 | 2 | 0 | 3 | 2 | 2 | 0 | 0 |
| $CH_3-N(S-CFCl_2)-CO-O-N=C(CH_3)(C_4H_9\text{-tert.})$ (19) | | 0 | 0 | 0 | 0 | 1 | 1 | 0 | 0 | — |
| $\text{phenyl-}N(S-CFCl_2)-CO-O-N=C(CH_3)(C_4H_9\text{-tert.})$ (20) | | 0 | 0 | 2 | 0 | 0 | 1 | 0 | 0 | 0 |
| $\text{phenyl-}N(S-CFCl_2)-CO-O-N=\text{cyclohexyl}$ (23) | | 0 | 0 | 0 | 0 | 0 | — | 0 | 0 | 1 |
| $CH_3-N(S-CFCl_2)-CO-O-N=C(\text{2-Cl-phenyl})(CN)$ (32) | | 0 | 0 | 0 | 0 | 0 | — | 0 | 0 | 2 |
| $\text{Cl-phenyl-}N(S-CFCl_2)-CO-O-N=C(CH_3)(CH_3)$ (5) | | 0 | 0 | 0 | 0 | 0 | — | 0 | 0 | 2 |
| $\text{2-Cl-phenyl-}N(S-CFCl_2)-CO-O-N=C(CH_3)(CH_3)$ (6) | | 0 | 0 | 0 | 0 | 0 | — | 0 | 0 | 0 |
| $\text{2,3-diCl-phenyl-}N(S-CFCl_2)-CO-O-N=C(CH_3)(CH_3)$ (7) | | 0 | 0 | 0 | 0 | 2 | — | 1 | 0 | — |
| $\text{Cl-phenyl-}N(S-CFCl_2)-CO-O-N=\text{cyclohexyl}$ (25) | | 0 | 0 | 0 | 0 | 2 | — | — | — | — |
| $\text{Cl-phenyl-}N(S-CFCl_2)-CO-O-N=\text{cyclohexyl}$ (26) | | 0 | 0 | 0 | 0 | 0 | — | 2 | 0 | 0 |
| $\text{2-Cl-phenyl-}N(S-CFCl_2)-CO-O-N=\text{cyclohexyl}$ (48) | | 0 | 1 | 0 | 0 | 2 | — | 2 | 0 | — |

Table 1-continued

| Active compounds | Active compound concentration ppm 10 | Mycelium growth test | | | | | | | |
|---|---|---|---|---|---|---|---|---|---|
| | | Piricularia oryzae | Phialophoracinerescens | Pellicularia sasakii | Fungi and bacteria | | | | |
| | | | | | Mycosphaerella muscola | Verticillium alboatrum | Fusarium dianthi | Cochliobolus miyabeanus | Colletotrichum coffeanum | Xanthomonas oryae |
| 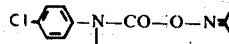 (45) | | 0 | 1 | 0 | 0 | 1 | — | 2 | 0 | 0 |
| 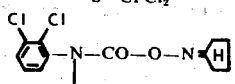 (46) | | 0 | 2 | 0 | 0 | 2 | — | 2 | 1 | — |

EXAMPLE 2

Piricularia test and Pellicularia test

Solvent: 1.9 parts by weight of dimethylformamide
Dispersing agent: 0.1 part by weight of alkylaryl polyglycol ether
Water: 98 parts by weight The amount of active compound required for the desired concentration of active compound in the spray liquor was mixed with the stated amount of solvent and of dispersing agent and the concentrate was diluted with the stated amount of water.

2 × 30 rice plants about 2–4 weeks old were sprayed with the spray liquor until dripping wet. The plants remained in a greenhouse at temperatures of 22° – 24°C and a relative atmospheric humidity of about 70% until they were dry. Thereafter, some of the plants were inoculated with an aqueous suspension of 100,000 to 200,000 spores/ml of *Piricularia oryzae* and placed in a chamber at 24°–26°C and 100% relative atmospheric humidity. The other plants were infected with a culture of *Pellicularia sasakii* grown on malt agar and were set up at 28–30°C and 100% relative atmospheric humidity. 5–8 days after the inoculation, the infection of all the leaves present at the time of inoculation with *Piriculeria oryzae* was determined as a percentage of the untreated, but also inoculated, control plants. In the case of the plants infected with *Pellicularia sasakii*, the infection on the leaf sheaths after the same time was determined, again in relation to the untreated but infected control. 0% means no infection and 100% means that the infection was exactly as great as in the case of the control plants.

The active compounds, active compound concentrations and results can be seen from the table which follows:

Table 2

| | *Piricularia* (a) and *Pellicularia* (b) test | | | | | |
|---|---|---|---|---|---|---|
| | Infection in % of the infection of the untreated control at an active compound concentration (in %) of | | | | | |
| | (a) | | | | (b) | |
| Active compound | 0.05 | 0.025 | 0.01 | 0.005 | 0.05 | 0.025 |
| 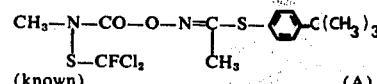 (A) (known) | 100 | | | | 100 | |
| 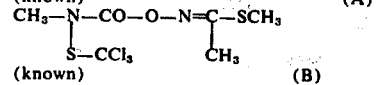 (B) (known) | 100 | | | | 100 | |
| 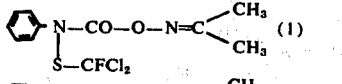 (1) | 0 | 0 | | | 0 | 100 |
| 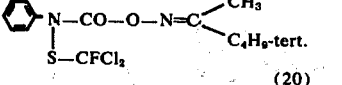 (20) | 0 | 58 | | | | |
| 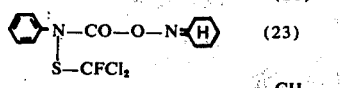 (23) | 0 | 0 | 0 | 50 | | |
| 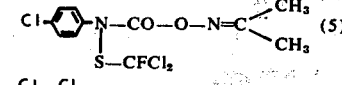 (5) | | 0 | | | | 50 |
| 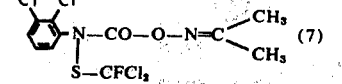 (7) | | 25 | | | | 50 |

EXAMPLE 3

Fusicladium test (apple scab) (Protective)

Solvent: 4.7 parts by weight of acetone
Emulsifier: 0.3 part by weight of alkylaryl polyglycol ether Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20°C and at a relative atmospheric humidity of 70%. They were then inoculated with an aqueous conidium suspension of the apple scab causative organism (*Fusicladium dendriticum Fuckel*) and incubated for 18 hours in a humidity chamber at 18°–20°C and at a relative atmospheric humidity of 100%.

The plants were then brought into a greenhouse for 14 days.

15 days after inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table:

Table 3

Fusicladium test/protective

| Active compound | Infection in % of the infection of the untreated control at an active compound concentration (in %) of 0.025 |
|---|---|
| $CH_3-N-CO-O-N=C-CH_3$ with $S-CCl_3$ and $S-C_2H_5$ (known) (C) | 45 |
| $CH_3-N-CO-O-N=C-S-CH_2-\phi$ with $S-CFCl_2$ and $CH_3$ (known) (D) | 42 |
| $CH_3-N-CO-O-N=C-S-\phi-Cl$ with $S-CFCl_2$ and $CH_3$ (known) (E) | 42 |
| $CH_3-N-CO-O-N=C-S-CH_2-\phi-NO_2$ with $S-CFCl_2$ and $CH_3$ (known) (F) | 83 |
| $CH_3-N-CO-O-N=C-\phi$ with $S-CFCl_2$ and $CN$ (2) | 0 |
| $\phi-N-CO-O-N=C(CH_3)_2$ with $S-CFCl_2$ (1) | 0 |
| $\phi-N-CO-O-N=\langle H \rangle$ with $S-CFCl_2$ (28) | 0 |
| $CH_3-N-CO-O-N=C(CH_3)(CO-OC_2H_5)$ with $S-CFCl_2$ (10) | 0 |
| $\phi-N-CO-O-N=C(CH_3)(CO-OC_2H_5)$ with $S-CFCl_2$ (11) | 0 |
| $CH_3-N-CO-O-N=\langle \rangle$ with $S-CFCl_2$ (17) | 0 |
| $\phi-N-CO-O-N=\langle \rangle$ with $S-CFCl_2$ (18) | 16 |
| $CH_3-N-CO-O-N=C(CO-OC_2H_5)_2$ with $S-CFCl_2$ (14) | 7 |
| $\phi-N-CO-O-N=C(CH_3)(C_4H_9\text{-tert.})$ with $S-CFCl_2$ (20) | 0 |
| $\phi-N-CO-O-N=\langle H \rangle$ with $S-CFCl_2$ (23) | 3 |

Table 3-continued

Fusicladium test/protective

| Active compound | Infection in % of the infection of the untreated control at an active compound concentration (in %) of 0.025 |
|---|---|
| 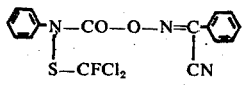 (30) | 17 |
| 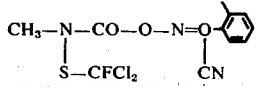 (32) | 0 |

EXAMPLE 4

Microbicidal action/reciprocal germinal inhibition values

The germinal inhibition values shown in the table indicate the concentrations which still suffice to inhibit growth.

Diluent: ethyleneglycol.

Table 4

Microbicidal action/reciprocal germinal inhibition values

| Active compound | Aspergillus terreus | Penicillium camerunense | Paecilomyces varioti | Trichophyton mentagrophytes | Candida albicans | Saccharomyces spec. | Bacterium proteus | Staphylococcus | Pseudomonas aeruginosa | Escherichia coli |
|---|---|---|---|---|---|---|---|---|---|---|
| 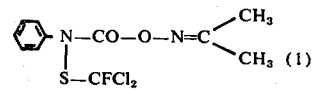 (1) | 26000 | 26000 | 26000 | 26000 | 26000 | 26000 | 26000 | 6000 | 13200 | 6000 |
| 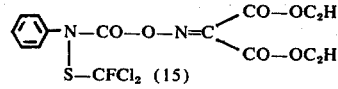 (15) | 13000 | 27000 | 27000 | 27000 | 27000 | 6900 | 13000 | 27000 | 27000 | 27000 |
| 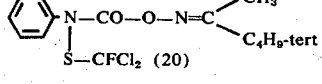 (20) | 15100 | 27000 | 27000 | 27000 | 6400 | 27000 | 27000 | 15100 | <6000 | 15100 |
| 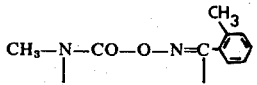 (47) | 13300 | 26000 | 26000 | 26000 | 26000 | 26000 | 15000 | 15000 | <5400 | 15000 |

The table shows the reciprocal germinal inhibition values for some selected varieties from the two groups of bacteria and fungi. These values express the dilutions of the stated compounds at which the growth of the selected micro-organisms is completely inhibited when these compounds are added to an optimum nutrient medium for the organisms. The micro-organisms employed for this inhibition test are wide-spread and known to be resistant to conventional chemical preservatives and to disinfectants.

The germinal inhibition values listed were determined according to the customary dilution methods, as follows.

The preparations to be tested, in the diluents stated, were set up at various concentrations. Certain quantities of the previously dissolved preparation were added to the previously prepared test tubes, filled with standardized nutrient substrates.

All work was carried out under sterile conditions. The various micro-organisms shown in the table were incubated at 30°C.

EXAMPLE 5

Microbicidal action/preservation of wood pulp

To carry out the experiments, wood pulp with the water content indicated in the table was treated, at various concentrations. Pieces of size 2 × 2 cm were placed on nutrient media inoculated with fungi, and incubated, and thereafter the inhibition zones were measured. Additionally, pieces of size 10 × 10 cm were buried in soil and the degree of rotting was observed after 3 and 6 weeks.

The concentrations shown in the table which follows relate to the dry weights.

The numerical values shown under the heading "Degree of rotting" denote:

0 no visible rotting
1 moderate attack by mold
2 strong attack by mold
3 complete rotting Table 5

| Active compound | Concentration | Inhibition zones in mm Aspergillus terreus | Penicillium camerunense | Degree of rotting after weeks 3 | 6 |
|---|---|---|---|---|---|
| (Control) | | 0 | 0 | 3 | |
| Phenyl-mercury acetate (known) | 1.6 g/kg | 5 | — | 1 | 1–2 |
| 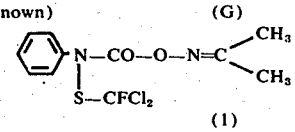 (1) | 1.6 g/kg | 12 | — | 2 | 3 |

Microbicidal action/preservation of wood pulp
Water content of the wood pulp: 50%

EXAMPLE 6

Microbicidal action/preservation of paints

The active compounds were added directly to the paint.

The requisite concentrations (g of active compound per liter of paint batch) can be seen from the table.

In the table the symbols denote:
− no deterioration due to micro-organisms
+ deterioration due to micro-organisms The assessment was made by smearing onto nutrient media after 24, 48 or 72 hours and subsequently incubating.

Table 6

Microbicidal action/preservation of paints

| Active compound | Concentration in the paint, g/l | Deterioration by micro-organisms after 24 | 48 | 72 hours |
|---|---|---|---|---|
| Control | | + | + | + |
| Cl-C6H3(CH3)-OH (known) | 1 | + | + | + |
| | 1.5 | − | + | + |
| | 2 | − | − | − |
| CH₃—N(S—CFCl₂)—CO—O—N=C(CN)(CO₂C₂H₅) (H) (12) | 0.25 | − | − | − |
| | 0.5 | − | − | − |
| | 0.75 | − | − | − |
| 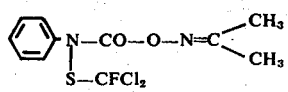—N(S—CFCl₂)—CO—O—N=C(CO—OC₂H₅)(CO—OC₂H₅) (15) | 0.25 | + | + | + |
| | 0.5 | − | − | − |
| | 0.75 | − | − | − |

The process of this invention is illustrated in the following preparative Examples.

EXAMPLE 7

C₆H₅—N(S—CFCl₂)—CO—O—N=C(CH₃)(CH₃)   (1)

27 g (0.1 mole) of N-(fluorodichloromethylthio)-N-phenylcarbamic acid fluoride and 7.3 g (0.1 mole) of acetono-oxime were dissolved in 100 ml of dioxane 12 g (0.12 mole) of triethylamine wer added dropwise thereto, while stirring, and the temperature was allowed to rise to 30°C. When the reaction had subsided, the reaction mixture was introduced into ice-water and the crystals formed thereby were filtered off and recrystallized, after drying, from petroleum ether. 27 g of N-(fluorodichloromethylthio)-N-phenylcarbamic acid acetonoxime ester of melting point 93°–95°C were obtained; this represented 83% of theory.

EXAMPLE 8

CH₃—N(S—CFCl₂)—CO—O—N=C(C₆H₅)(CN)   (2)

14.6 g (0.1 mole) of α-oximinophenylacetonitrile and 21 g (0.1 mole) of N-(fluorodichloromethylthio)-N-methylcarbamic acid fluoride were dissolved in 100 ml of dioxane and 12 g (0.12 mole) of triethylamine were added dropwise at room temperature. In the course thereof, the temperature rose to about 30°C. After the reaction, cold water was added and the crystals thereby produced were filtered off. After drying, 31 g of N-(fluorodichloromethylthio)-N-methylcarbamic acid phenylacetonitrile-oxime ester of melting point 93°c were obtained; this represented 92% of theory.

The following compounds of the general formula (I) were also prepared in a similar manner to that described above:

| Compound No. | Formula | Physical properties (refractive index: melting point in °C) |
|---|---|---|
| (3) | CH$_3$—N(—S—CCl$_3$)—CO—O—N=C(CH$_3$)(CH$_3$) | $n_D^{20}$ = 1.5268 |
| (4) | C$_6$H$_5$—N(—S—CCl$_3$)—CO—O—N=C(CH$_3$)(CH$_3$) | melting point 103–104 |
| (5) | 4-Cl-C$_6$H$_4$—N(—S—CFCl$_2$)—CO—O—N=C(CH$_3$)(CH$_3$) | melting point 104 |
| (6) | 2-Cl-C$_6$H$_4$—N(—S—CFCl$_2$)—CO—O—N=C(CH$_3$)(CH$_3$) | melting point 60–63 |
| (7) | 2,3-Cl$_2$-C$_6$H$_3$—N(—S—CFCl$_2$)—CO—O—N=C(CH$_3$)(CH$_3$) | melting point 80–82 |
| (8) | CH$_3$—N(—S—CFCl$_2$)—CO—O—N=C((CH$_2$)$_{16}$CH$_3$)((CH$_2$)$_{16}$CH$_3$) | $n_D^{20}$ = 1.4784 |
| (9) | C$_6$H$_5$—N(—S—CFCl$_2$)—CO—O—N=C((CH$_2$)$_{16}$CH$_3$)((CH$_2$)$_{16}$CH$_3$) | $n_D^{20}$ = 1.4968 |
| (10) | CH$_3$—N(—S—CFCl$_2$)—CO—O—N=C(CH$_3$)(CO—OC$_2$H$_5$) | $n_D^{20}$ = 1.4972 |
| (11) | C$_6$H$_5$—N(—S—CFCl$_2$)—CO—O—N=C(CH$_3$)(CO—OC$_2$H$_5$) | $n_D^{20}$ = 1.5428 |
| (12) | CH$_3$—N(—S—CFCl$_2$)—CO—O—N=C(CN)(CO$_2$H$_5$) | $n_D^{20}$ = 1.4970 |
| (13) | CH$_3$—N(—S—CFCl$_2$)—CO—O—N=C((CH$_2$)$_2$CO$_2$C$_2$H$_5$)((CH$_2$)$_2$CO$_2$C$_2$H$_5$) | $n_D^{20}$ = 1.4890 |
| (14) | CH$_3$—N(—S—CFCl$_2$)—CO—O—N=C(CO—OC$_2$H$_5$)(CO—OC$_2$H$_5$) | $n_D^{20}$ = 1.4855 |
| (15) | C$_6$H$_5$—N(—S—CFCl$_2$)—CO—O—N=C(CO—OC$_2$H$_5$)(CO—OC$_2$H$_5$) | $n_D^{20}$ = 1.5310 |
| (16) | C$_6$H$_5$—N(—S—CFCl$_2$)—CO—O—N=(cyclopentylidene) | melting point 77–79 |
| (17) | CH$_3$—N(—S—CFCl$_2$)—CO—O—N=(cyclohexylidene) | melting point 47–49 |
| (18) | C$_6$H$_5$—N(—S—CFCl$_2$)—CO—O—N=(cyclohexylidene) | melting point 94–97 |
| (19) | CH$_3$—N(—S—CFCl$_2$)—CO—O—N=C(CH$_3$)(C$_4$H$_9$-tert.) | $n_D^{20}$ = 1.4895 |
| (20) | C$_6$H$_5$—N(—S—CFCl$_2$)—CO—O—N=C(CH$_3$)(C$_4$H$_9$-tert.) | melting point 81 |
| (21) | C$_6$H$_5$—N(—S—CFCl$_2$)—CO—O—N=(cyclohexylidene-cyclohexyl) | melting point 95–98 |
| (22) | CH$_3$—N(—S—CFCl$_2$)—CO—O—N=(cyclohexylidene) | melting point 47–50 |
| (23) | C$_6$H$_5$—N(—S—CFCl$_2$)—CO—O—N=(cyclohexylidene) | melting point 65–67 |
| (24) | CH$_3$—N(—S—CCl$_3$)—CO—O—N=(cyclohexylidene) | melting point 71–75 |

-continued

| Compound No. | Formula | Physical properties (refractive index: melting point in °C) |
|---|---|---|
| (25) | Cl–C₆H₄–N(S–CFCl₂)–CO–O–N=(C₆H₁₀)–OH | melting point 83–86 |
| (26) | Cl–C₆H₄–N(S–CFCl₂)–CO–O–N=(C₆H₁₁) | melting point 89–91 |
| (27) | C₆H₅–N(S–CCl₃)–CO–O–N=(C₆H₁₁) | melting point 80–83 |
| (28) | C₆H₅–N(S–CFCl₂)–CO–O–N=(C₅H₉) | $n_D^{20} = 1.5771$ |
| (29) | CH₃–N(S–CCl₃)–CO–O–N=C(CN)–C₆H₅ | melting point 90–92 |
| (30) | C₆H₅–N(S–CFCl₂)–CO–O–N=C(CN)–C₆H₅ | melting point 90–91 |
| (31) | C₆H₅–N(S–CCl₃)–CO–O–N=C(CN)–C₆H₅ | melting point 99–101 |
| (32) | CH₃–N(S–CFCl₂)–CO–O–N=C(CN)–C₆H₄–Cl | $n_D^{20} = 1.5442$ |
| (33) | CH₃–N(S–CFCl₂)–CO–O–N=C(CN)–C₆H₄–CH₃ | $n_D^{20} = 1.5561$ |
| (34) | Cl–C₆H₄–N(S–CFCl₂)–CO–O–N=C(CN)–C₆H₄–CH₃ | melting point 125 |
| (35) | CH₃–N(S–CCl₃)–CO–O–N=C(CN)–C₆H₄–CH₃ | $n_D^{20} = 1.5647$ |
| (36) | CH₃–N(S–CCl₃)–CO–O–N=C(CN)–C₆H₄–Cl | melting point 70–72 |
| (37) | C₆H₅–N(S–CFCl₂)–CO–O–N=C(CN)–C₆H₄–CH₃ | melting point 87 |
| (38) | C₆H₅–N(S–CFCl₂)–CO–O–N=C(CN)–C₆H₄–Cl | $n_D^{20} = 1.5750$ |
| (39) | Cl–C₆H₄–N(S–CFCl₂)–CO–O–N=C(CN)–C₆H₅ | melting point 108 |
| (40) | (o-Cl)C₆H₄–N(S–CFCl₂)–CO–O–N=C(CN)–C₆H₅ | melting point 91–92 |
| (41) | C₆H₅–N(S–CFCl₂)–CO–O–N=C(CN)–C₄H₉-tert. | melting point 71–72 |
| (42) | C₆H₅–N(S–CCl₃)–CO–O–N=C(CN)–C₄H₉-tert. | melting point 79–81 |
| (43) | Cl–C₆H₄–N(S–CFCl₂)–CO–O–N=C(CN)–C₄H₉-tert. | melting point 110–111 |
| (44) | C₆H₅–N(S–CFCl₂)–CO–O–N=C[(CH₂)₂–COOC₂H₅][(CH₂)₂–COOC₂H₅] | $n_D^{20} = 1.5242$ |

| Compound No. | Formula | Physical properties (refractive index: melting point in °C) |
|---|---|---|
| (45) | Cl-C₆H₄-N(S-CFCl₂)-CO-O-N=C(H)(cyclohexyl) | |
| (46) | 2,3-Cl₂-C₆H₃-N(S-CFCl₂)-CO-O-N=C(H)(cyclohexyl) | $n_D^{20} = 1.5771$ |
| (47) | CH₃-N(S-CFCl₂)-CO-O-N=C(CH₃)(C₆H₄-CN) | $n_D^{20} = 1.5561$ |
| (48) | 2-Cl-C₆H₄-N(S-CFCl₂)-CO-O-N=(cyclohexyl with H) | |

Other compounds which can be similarly prepared include:

(49) C₆H₁₁-N(S-CF₂Cl)-CO-O-N=C(CH₃)(CH₂-CH₂-CO-NH₂)

(50) 4-NO₂-C₆H₄-N(S-CFCl₂)-CO-O-N=C(CH=C(H)(CH₃))(CH₃)·CH₃

(51) 3-iC₃H₇-C₆H₄-N(S-CFCl₂)-CO-O-N=C(CH₃)(C₆H₄-CN)

(52) 2-F₃C-C₆H₄-N(S-CFCl₂)-CO-O-N=C(C₂H₅)(C₆H₄-NO₂)

(53) 4-C₄H₉O-C₆H₄-N(S-CFCl₂)-CO-O-N=C(CH₃)(C₆H₄-CF₃)

(54) CH₃-N(S-CF₃)-CO-O-N=C(C₂H₅)(2-OCH₃-6-CH₃-C₆H₃)

(55) C₂H₅-N(S-CF₂Cl)-CO-O-N=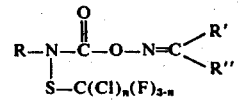C₄H₉ tert.

(56) C₂H₅-N(S-CFCl₂)-CO-O-N=(cyclohexyl-H)-CH(CH₃)(CH₃)

and the like.

It will be appreciated that the instant specification and examples are set forth by way of illustration and not limitation, and that various modifications and changes may be made without departing from the spirit and scope of the present invention.

What is claimed is:

1. An N-(trihalomethylthio)carbamic acid oxime ester of the formula $$R-N(S-C(Cl)_n(F)_{3-n})-\overset{O}{\overset{\|}{C}}-O-N=C\overset{R'}{\underset{R''}{}}$$

in which

R is alkyl of up to 4 carbon atoms; or phenyl optionally carrying at least one halogen, nitro, $C_1-C_6$ alkyl, trifluoromethyl or $C_1-C_6$ alkoxy radical;

R' is alkyl or alkenyl of up to 20 carbon atoms optionally substituted by an alkoxycarbonyl with a total of up to 5 carbon atoms or an amidocarbonyl radical; cyclohexyl; phenyl optionally carrying at least one halogen, nitro, trifluoromethyl, $C_1-C_6$ alkyl or $C_1-C_6$ alkoxy radical; halogen; alkoxycarbonyl with a total of up to 7 carbon atoms; or amidocarbonyl;

R'' is alkyl or alkenyl of up to 20 carbon atoms substituted by an alkoxycarbonyl with a total of up to 5 carbon atoms; or alkoxycarbonyl with a total of up to 7 carbon atoms; and n is 0, 1, 2 or 3.

2. A compound according to claim 1, in which

R is alkyl of up to 4 carbon atoms, or phenyl optionally substituted by fluorine, chlorine, nitro, methyl, trifluoromethyl or methoxy;

n is 1, 2 or 3; and

R" is alkyl of up to 20 carbon atoms substituted by alkoxycarbonyl with a total of up to 5 carbon atoms; or alkoxycarbonyl with a total of up to 7 carbon atoms.

3. A compound according to claim 1, in which
R is methyl, phenyl or chlorophenyl,
n is 2 or 3, and
R' and R" each individually is alkyl substituted by lower alkoxycarbonyl, or lower alkoxycarbonyl.

4. A compound according to claim 1, wherein such compound is N-(fluorodichloromethylthio)-N-phenyl-carbamic acid ethylacetoacetate-oxime ester of the formula

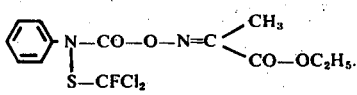

5. A compound according to claim 1, wherein such compound is N-(fluorodichloromethylthio)-N-methyl carbamic acid ethylacetoacetate-oxime ester of the formula

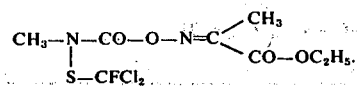

6. A compound according to claim 1, wherein such compound is N-(fluorodichloromethylthio)-N-methyl-carbamic acid diethyl-γ-ketopimelate-oxime ester of the formula

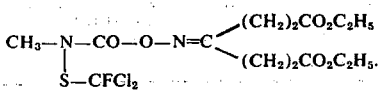

7. A compound according to claim 1, wherein such compound is N-(fluorodichloromethylthio)-N-methyl-carbamic acid diethyl-γ-ketomalonate-oxime ester of the formula

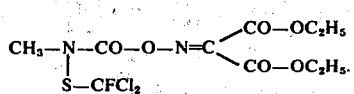

8. A compound according to claim 1, wherein such compound is N-(fluorodichloromethylthio)-N-phenyl-carbamic acid diethyl-γ-ketomalonate-oxime ester of the formula

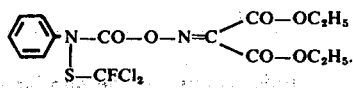

9. A compound according to claim 1, wherein such compound is N-(fluorodichloromethylthio)-N-phenyl-carbamic acid diethyl-γ-ketopimelate-oxime ester of the formula

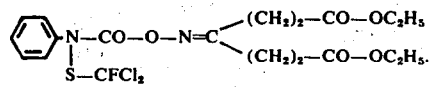

* * * * *